(12) United States Patent
Chien et al.

(10) Patent No.: US 6,629,952 B1
(45) Date of Patent: Oct. 7, 2003

(54) HIGH PRESSURE VASCULAR BALLOON CATHETER

(75) Inventors: Thomas Y. Chien, San Jose, CA (US); Hanh Doan, Milpitas, CA (US); Hong Doan, San Jose, CA (US); Susan C. Simeon, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/751,534

(22) Filed: Dec. 29, 2000

(51) Int. Cl.⁷ .................. A61M 31/00; A61M 37/00
(52) U.S. Cl. .................. 604/103.09; 606/194
(58) Field of Search .................. 604/96.01, 103, 604/103.06, 103.08, 103.09, 523–527, 915, 917, 921; 606/108, 192, 194

(56) References Cited

U.S. PATENT DOCUMENTS

| | | | |
|---|---|---|---|
| 3,416,531 A | 12/1968 | Edwards | 128/348 |
| 4,676,229 A | 6/1987 | Krasnicki et al. | 128/4 |
| 4,806,182 A | 2/1989 | Rydell et al. | 156/211 |
| 4,899,787 A | 2/1990 | Ouchi et al. | 138/131 |
| 4,981,478 A | 1/1991 | Evard et al. | 604/282 |
| 5,037,404 A | 8/1991 | Gold et al. | 604/282 |
| 5,057,092 A | 10/1991 | Webster, Jr. | 604/282 |
| 5,069,674 A | 12/1991 | Fearnot et al. | 604/282 |
| 5,176,660 A | 1/1993 | Truckai | 604/282 |
| 5,178,158 A | 1/1993 | de Toledo | 128/772 |
| 5,180,376 A | 1/1993 | Fischell | 604/282 |
| 5,313,967 A | 5/1994 | Lieber et al. | 128/772 |
| 5,728,065 A * | 3/1998 | Follmer et al. | |
| 5,906,606 A * | 5/1999 | Chee et al. | |
| 6,123,718 A | 9/2000 | Tu et al. | 607/113 |
| 6,129,707 A | 10/2000 | Cryer | 604/96.01 |
| 6,135,992 A | 10/2000 | Wang | 604/525 |
| 6,152,912 A | 11/2000 | Jansen et al. | 604/526 |
| 6,152,914 A | 11/2000 | Van De Kerkhof et al. | 604/533 |

* cited by examiner

Primary Examiner—LoAn H. Thanh
(74) Attorney, Agent, or Firm—Crompton, Seager & Tufte, LLC (57) ABSTRACT

The present invention relates to a high pressure vascular balloon catheter wherein the walls of the tube attached to the balloon-forming segment are reinforced with a braided ribbon member. The walls of the inner tube that provides the lumen for a guidewire may also be reinforced in the same way. The reinforcement has the dual effect of providing strength against rupture under pressure and prevention of ovalizing or kinking during insertion into tortuous vessels of a vascular system.

23 Claims, 8 Drawing Sheets

HIGH PRESSURE VASCULAR BALLOON CATHETER

FIELD OF THE INVENTION

The present invention relates to the fields of mechanical engineering, materials science, medical device technology and medicine. In particular, it relates to a high pressure vascular balloon catheter having a high degree of flexibility together with high resistance to rupture from internal pressure created by balloon inflation.

BACKGROUND OF THE INVENTION

The following is presented for the purpose of understanding the context of the present invention and it is not to be construed and is not admitted to be prior art to this invention.

Catheters are being increasingly used to reach more and more remote locations in the body of a patient. When the target is a soft tissue site, the vascular system in the region often consists of vessels of very small diameter. The vessels also are often convoluted, making many sharp twist and bends. To navigate these small tortuous vessels requires a catheter having a correspondingly small outside diameter. The predominant method for achieving small diameters is to use catheters having very thin walls. However, as the walls of a catheter get thinner, they tend to lose their torsional and longitudinal rigidty. That is, while extraordinary flexibility is required to navigate the vessel of the vascular system, sufficient torsional rigidity must be maintained to permit steering of the catheter through the vessel and sufficient longitudinal rigidity must remain to allow the catheter to be advance—pushed—through the vessel. Furthermore, thin wall tubes have a tendency to crimp or kink when bent in a small radius. This can result in the binding of guidewires within the catheter thus frustrating further advancement of the catheter in the vessel which normally depends on prior advancement of a guidewire. A number of patents have been issued which purport to address torsional and longitudinal rigdity and kinking in thin-walled catheter tubes.

U.S. Pat. No. 4,676,229, to Krasnicki, et al. (1987), relates to a biopsy channel comprising a tubular substrate helically wound with a high strength wire filament, the winding being spaced sufficiently apart to provide regions between the windings into which a relatively softer elastomeric filler material can be interspersed. A top coating of a lubricious material covers the filler material. The resulting tubular structure is purportedly capable of tight radius bends without collapsing.

U.S. Pat. No. 4,981,478 to Evard, et al. (1991), relates to a vascular catheter having a tubular member of composite structure. The structure is comprised of a tubular substrate covered with a resin-impregnated fibrous material extending over a substantial part of the length of the tubular member. The fibers are epoxy-impregnated aramid or polyester multifilament fibers. The fibers are described as being either spiral wound or braided around the tubular member. This structure purportedly affords a tubular member with longitudinal flexibility and diametric rigidity, i.e., kink-resistance. The fiber-reinforced tube may be placed within a second tube, e.g., a tube having a balloon-forming region at its distal end such as an angioplasty catheter.

U.S. Pat. No. 5,037,404, to Gold, et al. (1991) relates to a flexible catheter design in which the longitudinal flexibility and torsional rigidity are controllable along the length of the catheter shaft by encasing the shaft in a tubular braided wire sheath in which the angle between the crossing strands of the braid varies. The change in angle is stated to result in a change in the torsional and longitudinal rigidity of the catheter shaft.

U.S. Pat. No. 5,057,092 to Webster (1991), provides another means for controlling the flexibility of a catheter shaft, in this case to generally reduce rather than increase it. The '092 patent discloses an elongated tubular body having an inner wall, a reinforcing braided tubular mesh interwoven with longitudinal warp strands surrounding the inner wall and an outer wall encasing the reinforcing structure between it and the inner wall. The modulus of elasticity of the longitudinal strands is lower than that of the helical mesh strands. This results, according to the patentee, in increased bending stiffness without a concomitant decrease in the resiliency of the catheter body.

U.S. Pat. No. 5,069,674, to Fearnot et al. (1991) describes a small diameter epidural catheter that is both flexible and kink-resistant. This is accomplished by expansion-fitting a wire coil inside a tubular sheath in which the ratio of the outside diameter of the wire coil to the cross-sectional diameter of the individual turns is within a range of 4 to 10. In this configuration, the wire coils are said to prevent the tubular sheath from rupturing or kinking when the catheter is flexed or bent.

U.S. Pat. No. 5,176,660, to Truckai (1993) discloses a catheter body consisting of at least one resilient tubular member in which the flexibility is controlled by wrapping the tubular layer in a sheath of helically-disposed crossing strands in which one of the strands is ribbon-like in cross-section and has a width that is 4 to 8 times its thickness. Other strands are circular in cross-section. A reinforcing filament generally parallel to the longitudinal axis of the tubular layer is also described. These various strand types and directional orientation is said to permit control of the torsional and longitudinal rigidity of the tubular member along the length of the catheter body.

U.S. Pat. No. 5,180,376, to Fischell (1993) describes an introducer sheath for an angioplasty or atherectomy catheter that consists of a thin, flat wire metal coil that is surrounded only on its exterior surface with a plastic coating. The claimed benefit of this design is to provide a sheath through which devices can be routed to a specific locus in a patient's body wherein the sheath is as thin as possible but has the strength to resist buckling when being pushed through the femoral artery.

U.S. Pat. No. 6,152,912, to Jarlsen, et al. (2000) teaches a catheter suitable for accessing a tissue target in a patient's body, the catheter having a reinforcing member wound within the catheter body to provide kink-resistance and controlled stiffness. The reinforcing member is comprises of a wire ribbon helically wound around an inner lubricious liner, the wire ribbon being helically back-wound over the top of the first winding on the more proximal portion of the assembly. The entire wire member is then over-coated with an outer layer of polymer.

The problem of achieving a small tube diameter while still having sufficient torsional and longitudinal control and kink resistance is compounded in cases where the use of a catheter comprised of more than one channel or tube is required such as in the treatment of atherosclerotic lesions in the arteries of the brain using a balloon catheter similar to, but necessarily much smaller than, that employed for percutaneous transluminal coronary angioplasty. Such a catheter is composed of two tubes, an outer tube that, at or near its distal end, is capable of being expanded to form a balloon-like structure and an inner tube through which a guide wire or other instrumentation may be passed. The annular space between the two tubes provides a channel through which liquids can be introduced and removed to inflate and deflate the balloon.

The general approach to accommodating the need for smaller outside diameter catheters is to reduce the size of guide wires and the wall thickness of both tubes making up a balloon catheter. However, there are limits to the extent to which these dimensional reductions can be taken. If the diameter of the guidewire is reduced too much, the guidewire will lose its ability to effectively transmit torsional and axial forces necessary to steer and advance the guide wire through tortuous vascular systems. If the diameter of the wire is maintained at a functional dimension, then the remaining way to reduce overall catheter size is to reduce the wall thickness of the tubular portions of the catheters. As noted above, this can result in loss of cross-sectional circularity of either or both the inside and outside tubes, resulting in crimping or kinking. If the inner tube kinks, then the guidewire will become bound within the tube's lumen and can no longer be advanced through the vascular system. If the outer tube kinks, it may cause the inner to tube to close down and bind the guide wire or it may constrict, even close down, the annular space between the tubes making it impossible to expand and deflate the balloon structure.

The patents discussed above are directed to single tube catheters having controlled flexibility and kink resistance to permit traversing small vascular channels. However, none of the aforementioned designs provides a balloon catheter structure combining a very thin overall cross-section with controlled flexibility, kink resistance and the structural strength to withstand the high pressures created during the inflation of the balloon portion of the catheter. The present invention provides such a catheter.

SUMMARY OF THE INVENTION

Thus, in one aspect, the present invention relates to a high-pressure balloon catheter, comprising:

a first flexible elongate tubular member having a proximal end and a distal end, the first member having an outer surface and an inner surface that describes a lumen; a second flexible elongate tubular member having a proximal end and a distal end, the second elongate member being disposed within the lumen of the first elongate tubular member and extending distally beyond the distal end of the first elongate member, the second member having an inner surface describing a lumen and an outer surface describing an outer diameter that is less than an inner diameter of the first elongate member such that an annular lumen is formed between the first and second elongate members;

an inflatable balloon-forming structure having a proximal end and a distal end, the structure being sealably coupled at its proximal end to the distal end of the first elongated member and at it's distal end to the distal end of the second elongate member;

a first reinforcing member disposed between the inner and outer surfaces of the flexible portion of the first elongate member, the first reinforcing member comprising a plurality of strands, each strand having a width and a thickness; and, a second reinforcing member disposed between the inner and outer surfaces of the second flexible elongate member.

In another aspect, this invention relates to the above high pressure balloon catheter in which the first reinforcing member is a first braided reinforcing member.

It is also an aspect of this invention that, when the first reinforcing member is a braided reinforcing member, each of the strands of the braided reinforcing member have a width of from about 0.002 to about 0.004 inches.

In a further aspect, this invention relates to the above high pressure balloon catheter wherein each strand of the first braided reinforcing member has a thickness of from about 0.0004 to about 0.00075 inches.

Each strand of the first braided reinforcing member has a width of about 0.003 inches and a thickness of about 0.0005 inches in yet another aspect of this invention.

It is an aspect of this invention that the first reinforcing member is selected from the group consisting of a metal and a high tensile strength fiber.

The metal of which the first reinforcing member is constructed is selected from the group consisting of nitinol and stainless steel in a still further aspect of this invention.

The high tensile strength fiber of which the first reinforcing member is constructed is selected from the group consisting of aramid, vertran, liquid crystal polymer and carbon fiber in another aspect of this invention.

It is an aspect of this invention that the proximal end of the balloon-forming structure is sealably coupled to the distal end of the first flexible elongate member by a butt weld.

It is an aspect of this invention that, in the above butt-welded balloon forming structure, the first reinforcing member extends distally over the butt weld.

In yet another aspect of this invention, the first reinforcing member extends completely over the balloon-forming member to the distal end thereof.

The balloon-forming member has an inner surface and an outer surface, the first reinforcing member being disposed between the inner and outer surfaces from the proximal end of the balloon-forming structure to the distal end of the balloon-forming structure in a further aspect of this invention.

It is an aspect of this invention that the second reinforcing member extends from a point distal to the proximal end of the first reinforcing member to a point distal to the proximate end of the balloon-forming structure.

The second reinforcing member comprises a second braided reinforcing member in another aspect of this invention.

The second braided reinforcing member comprises a plurality of strands, each having a width and a thickness in an aspect of this invention.

Each strand of the second braided reinforcing member has a width of from about 0.002 to about 0.004 inches in a further aspect of this invention.

Each strand of the second braided reinforcing member has a thickness of from about 0.0004 to about 0.00075 inches in an aspect of this invention.

Each strand of the second braided reinforcing member has a width of about 0.003 inches and a thickness of about 0.0005 inches in a still further aspect of this invention.

It is an aspect of this invention that the second reinforcing member is selected from the group consisting of a metal and a high tensile strength fiber.

The metal from which the second reinforcing member is formed is selected from the group consisting of nitinol and stainless steel in an aspect of this invention.

The high tensile strength fiber from which the second reinforcing member is formed is selected from the group consisting of aramid, vertran, liquid crystal polymer and carbon fiber is an aspect of this invention.

In another aspect of this invention, a channel is located at the distal end of the balloon-forming structure where the structure is coupled to the distal end of the second elongated flexible member, the channel operatively coupling the interior of the balloon-forming structure with the external environment.

A further aspect of this invention is a high-pressure balloon catheter that, in addition to having the first and second reinforcing members described above, also comprises a balloon-forming structure having an inner and an outer surface wherein a third reinforcing member is disposed between the inner and outer surfaces from the distal end of the balloon-forming structure to a point proximal to the proximal end of the balloon-forming structure such that, when the proximal end of the balloon-forming structure is coupled to the distal end of the first elongate member, the third reinforcing member extends proximally over the coupling.

DETAILED DESCRIPTION OF THE INVENTION

DISCUSSION

Figure 1:
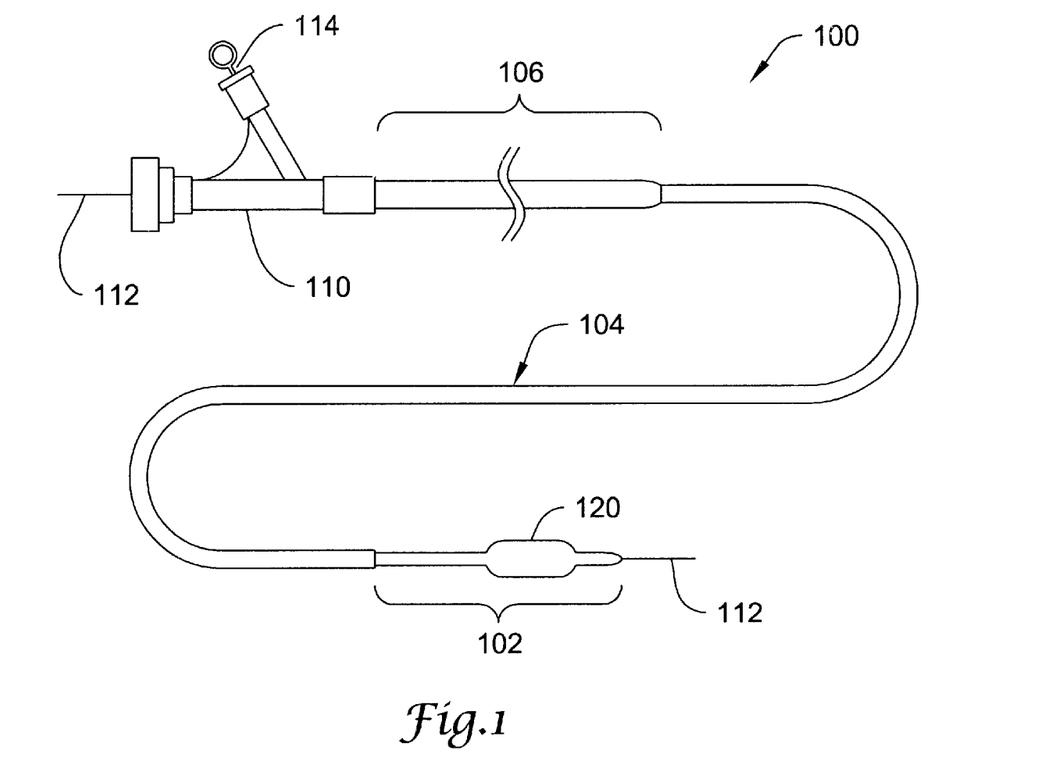
FIG. 1 is a surface depiction of a balloon catheter capable of incorporating the various aspects of this invention.

This invention relates to the distal portion of a balloon catheter. The distal portion is generally anywhere from the distal 2 cm to the distal 30 cm of the catheter although, depending on the tissue area to be reached, the distal end may be of any desired length and, regardless of the length, would be within the scope of this invention. The distal portion has a small over-all cross-section that allows it to be used to reach remote areas of tissue such as the brain and the liver. The small cross-section is achieved by reducing the wall thickness of both the tubes making up the catheter. Structural integrity of the outer tube, which is subjected to high pressures during inflation of the balloon-forming structure is maintained by incorporating a reinforcing member into the wall of the outer tube. In a presently preferred embodiment of this invention, the reinforcing member is comprised of braided strands. A braided reinforcing member provides kink resistance to the outer tube when the tube is being bent to traverse tortured pathways in the vascular system. The inner tube likewise includes a reinforcing member, the purpose of which is to provide structural integrity against kinking when the tube is being bent to conform to the shape of the outer tube. The inner reinforcing member is also a braided reinforcing member in a presently preferred embodiment of this invention, FIG. 1 is an exterior view of a typical balloon catheter 100. Catheter 100 is shown solely for the purpose of aiding in the understanding of the present invention and does not constitute the only assembly covered by this invention. Any manner of balloon catheter assembly incorporating the aspects of this invention is within the scope hereof. In any event, catheter 100 consists of a luer assembly 110 for guide-wire 112 manipulation and for liquid introduction into the balloon-forming structure 120. Within balloon-forming structure 120 are radiopaque regions (not shown) which permit visualization of the position of the distal end of the catheter in a patient's body. Catheter 100 is shown as having several portions 102, 104 and 106. These portions have differing degrees of flexibility with portion 106 being the lease flexible, portion 104 being intermediate in flexibility and portion 102 being the most flexible. A catheter of this invention, however, is not limited to any particular number of such portions and may have fewer than three areas of different flexibility or many more. As described with regard to catheter 100, in general, as one progresses toward the distal end of the catheter, the assembly becomes increasingly flexible. The present invention relates to the most distal and most flexible portion 102 of a balloon catheter.

Figure 2A:
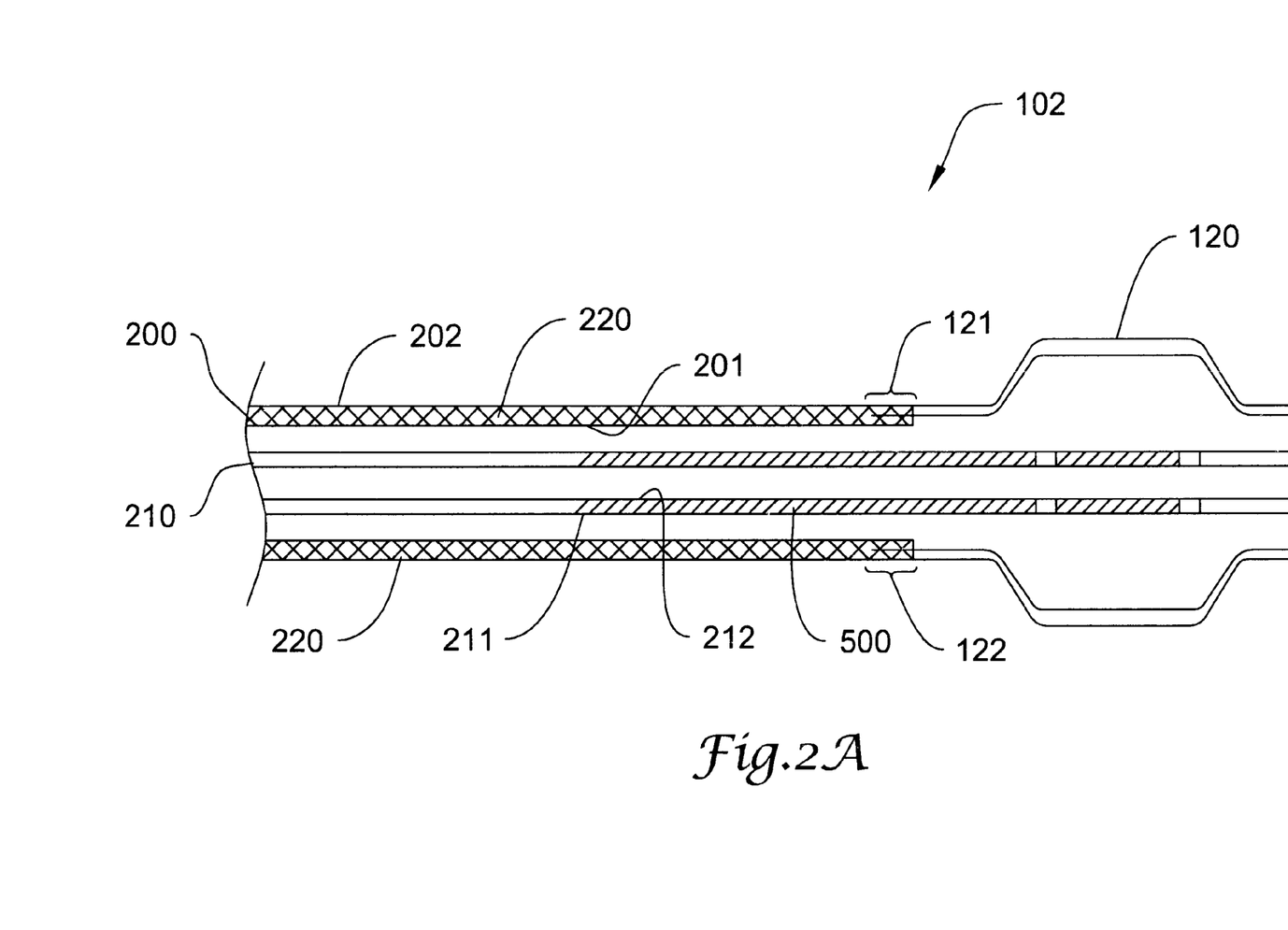
FIG. 2A is a schematic representation of the distal portion of the above catheter wherein various aspects of this invention are revealed.
Figure 2B:
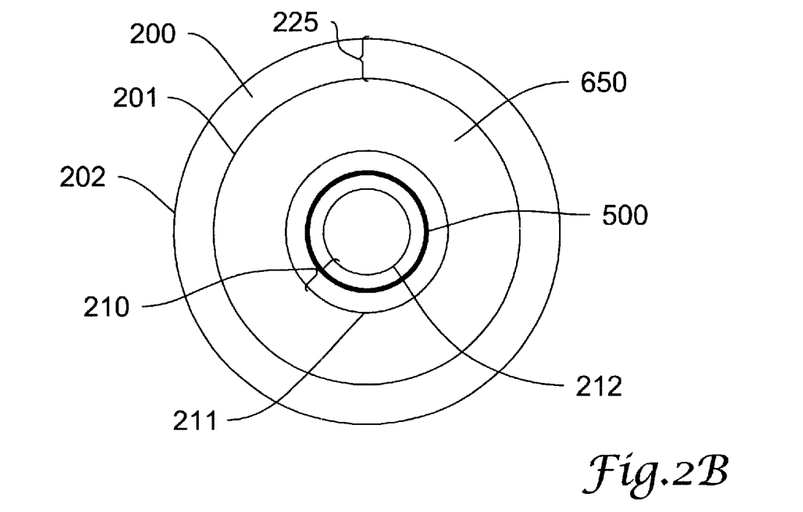
FIG. 2B is a schematic representation of a cross-section of the distal portion shown in FIG. 2A.

FIG. 2A is an isolated blow-up of portion 102 of catheter 100. Portion 102 comprises two tubular sheaths 200 an 210, tubular sheath 210 being disposed within tubular sheath 200 as shown in FIG. 2B. Each tubular sheath, hereinafter referred to simply as a "tube," has an inner and an outer surface. That is tube 200 has inner surface 201 and outer surface 202 and tube 210 has inner surface 212 and outer surface 211. The two surfaces of either tube may constructed of the same or of different materials. If they are comprised of different materials, then the tube is composed of layers with the inner surface of a tube comprising the surface of one layer and the outer surface of that tube comprising, a surface of another layer. That is, inner surface 201 of tube 200 may be comprises of a layer of material 201A and outer surface 202 may be comprised of a different layer of material 202A. The composition of tube 200 or tube 210 is not limited to two layers and there may optionally be additional layers of different materials between the layers having surfaces 201 and 202. A wide variety of materials may be used to make tubes 200 and 210. For example, without limitation, polytetrafluoroethylene (TEFLON), polyethylene, polypropylene, the nylons, polyesters, polyimides, polyamides and the like. Presently preferred polymers for use in manufacture of the various aspects of this invention are various PEBAX (polyether block amide) thermoplastic elastomer resins such as PEBAX 4033, PEBAX 5533 and PEBAX 6333, alone or in combination.

Disposed between surfaces 201 and 202 or layers 201A and 202 A is a reinforcing member. While the reinforcing member may have a number of different structures including, but not limited to, helically wound strands, longitudinal strands, etc., in a presently preferred embodiment of this invention the reinforcing member is a braided reinforcing member 220. Braided reinforcing member 220 is comprised of a plurality of strands 221 each having a ribbon-like structure, that is, each strand has a cross-section having a width 223 and a thickness 222 where the width is greater than the thickness as shown in FIG. 3B.

Figure 3A:
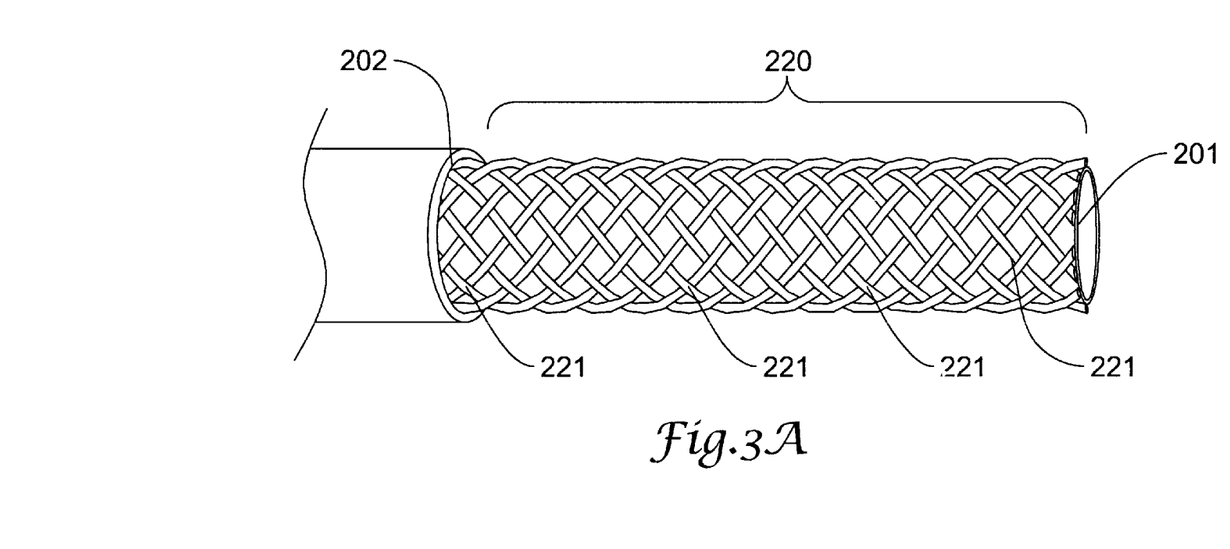
FIG. 3A is a schematic representation of a braided reinforcing member of this invention.
Figure 3B:
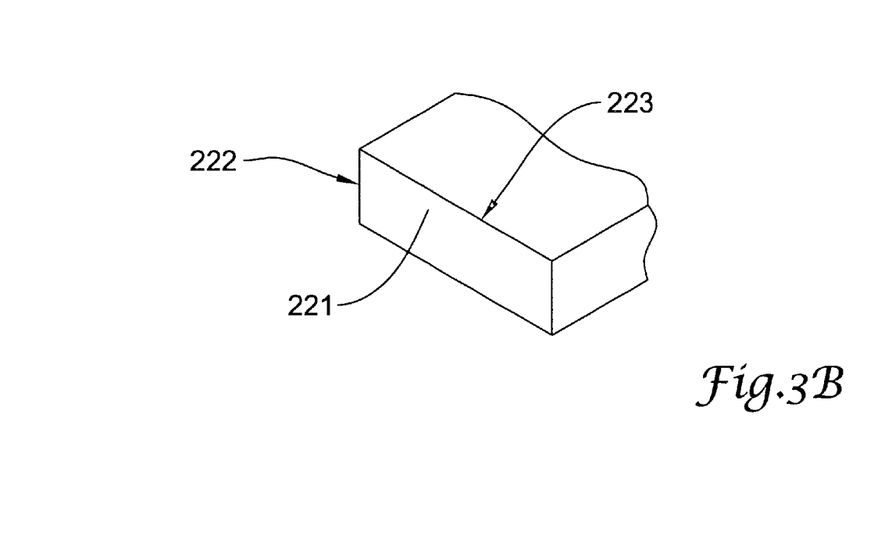
FIG. 3B is a schematic representation of a cross-section of a single strand of the braided reinforcing member shown in FIG. 3A.

FIG. 3 shows a blow-up of a portion of braided reinforcing member 220. Braided reinforcing member 220 is comprises of individual strands 221. Individual strands 221 may be constructed of a variety of different materials. They may be metallic or nonmetallic. Metals that may be used include, without limitation, stainless steel, platinum, palladium, gold, rhodium, tantalum and the like. Metal alloys may also be used such as, again without limitation, nitinol (a titanium/nickel alloy). Non-metallic substances that can be used include, without limitation, aramids (e.g., KEVLAR), liquid crystal polymers and carbon fibers.

When individual strands 221 are metallic or alloy, each strand 221 has a width 223 of from about 0.002 inches to about 0.004 inches with about 0.003 inches being presently preferred. The thickness 222 of such metallic strands 221 is from about 0.0004 to about 0.00075 inches with about 0.0005 inches being presently preferred.

Braided reinforcing member 220 is disposed between surface 201 and surface 202 of tube 200. If the surfaces are of the same materials, i.e., there are no layers of materials as discussed above, braided reinforcing member 220 may simply be embedded in the material of which tube 200 is constructed. Or, if surface 201 is of a different material than surface 202, that is, if tube 200 is composed of at least two layers of different materials, braided reinforcing member 220 may be sandwiched between any two layers. When tube 200 is constructed of layers of different materials, an adhesive may be placed between the layers to assist in binding braided reinforcing member 220 to the materials and the materials to one another.

In order to accommodate braided member 220 while maintaining as small an overall cross-section as possible, the thickness of the materials of which wall 225 of tube 200 (FIG. 2B) is comprised must be reduced. When tube 200 is made of a single material, this amounts to simply using less material to encapsulate braided member 220. When two or more different materials are used, the thickness of any of them may be reduced. In a presently preferred embodiment of this invention, inner layer 201A is necked down, which can be accomplished during the fabrication or some of the material can be removed by, for example, laser milling. Braided reinforcing member 220 can then simply be slid onto inner layer 201A and outer layer 202A can then be applied over the entire structure to encapsulate braided reinforcing member 220.

Figure 4:
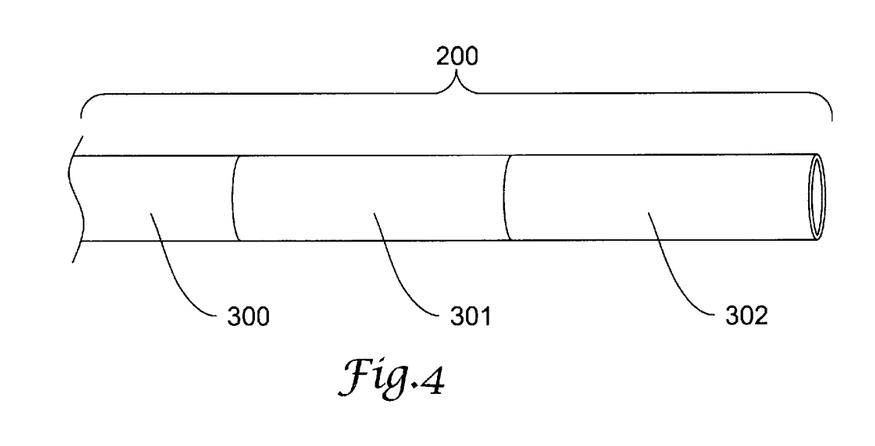
FIG. 4 is a schematic representation of a section of the outer tube comprising the distal end of a catheter of this invention wherein longitudinally varying the composition of the material from which the tube is formed is depicted.

It is also within the scope of this invention that each layer of tube 200 is constructed of different materials longitudinally. FIG. 4 shows such a structure wherein outer surface 202 is constructed of materials 300, 301 and 302 along its length.

As shown in FIG. 2, the distal end of catheter 100 comprises a balloon-forming structure 120. Balloon-forming structure 120 is shown in its inflated state in FIG. 2 and the other figures herein so as to more easily depict the aspects of the present invention. It is understood, however, that, in its deflated state, balloon-forming structure 120 compresses down until it has essentially the same profile, i.e., cross-section, as portion 102 of catheter 100 proximal to it.

Figure 5A:
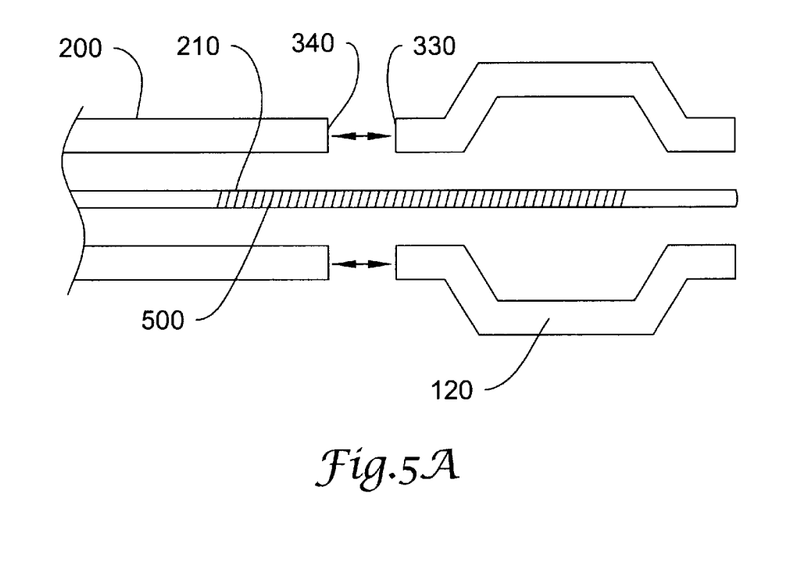
FIG. 5A is a schematic representation of the balloon-forming structure of a catheter of this invention about to be butt-welded to the outer tube of the body of the catheter.

Balloon-forming structure 120 is coupled at its proximal end to the distal end of outer tube 200. This may be accomplished by overlapping a proximal portion 121 of balloon-forming structure 120 with a distal portion of tube 200 and binding the two portions using an adhesive (FIG. 2A). In making this sort of connection, a bead 122 is usually created where the overlap occurs and the adhesive is applied (FIG. 2A). This bead may adversely affect the cross-sectional profile of the catheter. Thus, it is an aspect of this invention that the proximal end 330 of balloon-forming structure 120 is butt-welded to the distal end 340 of tube 200 as shown in FIG. 5A. This can be accomplished by, for example, laser welding.

Figure 5B:
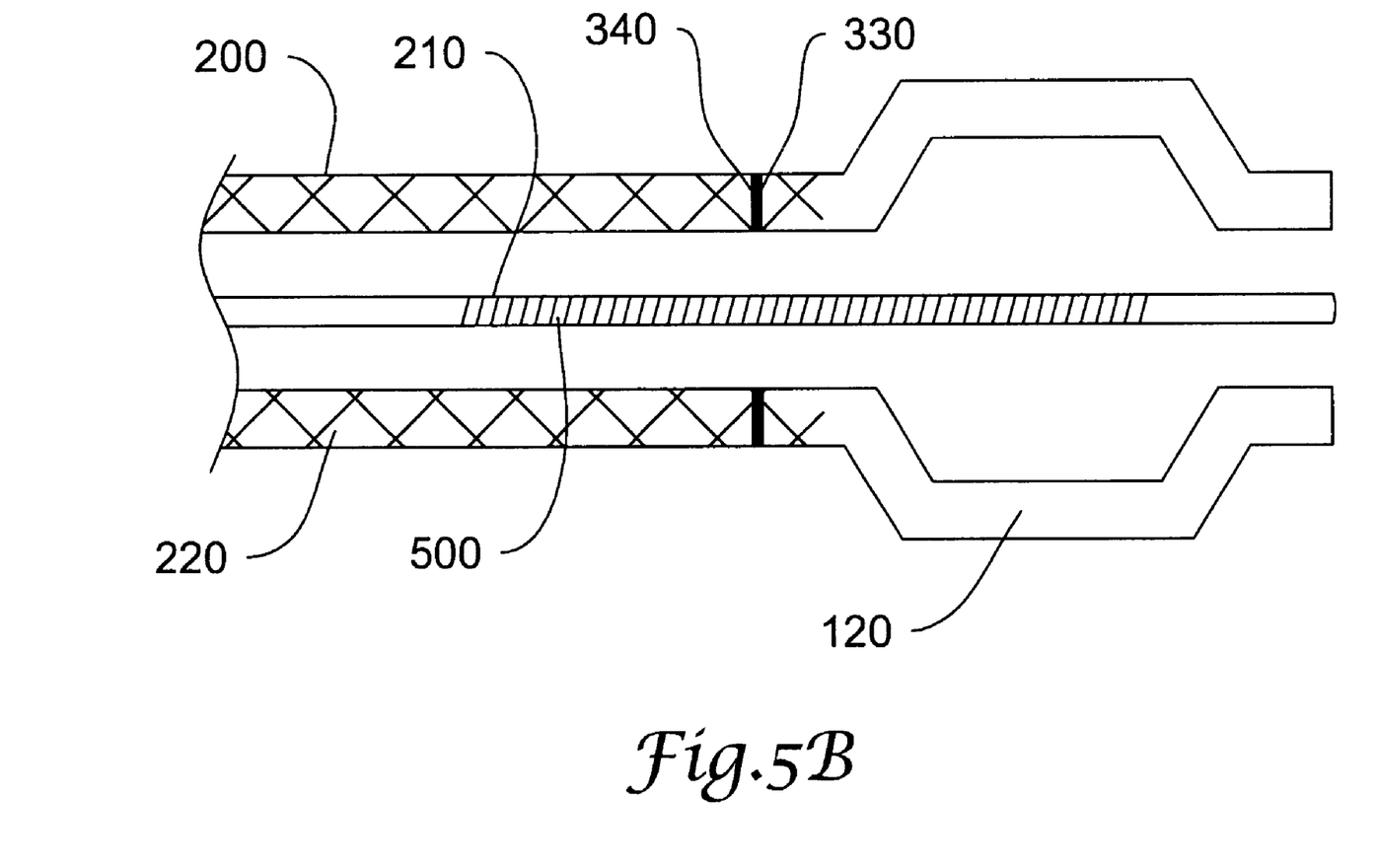
FIG. 5B is a schematic representation of a balloon-forming structure butt-welded to the outer tube of a catheter showing a braided reinforcing member of this invention overlapping the weld.

Regardless of whether balloon-forming structure 120 is overlapped and adhesively bonded to tube 200 or whether it is butt-welded to tube 200, braided reinforcing member 220 overlaps the joint as shown in FIG. 5B to add strength and rupture resistance to the joint.

Figure 6:
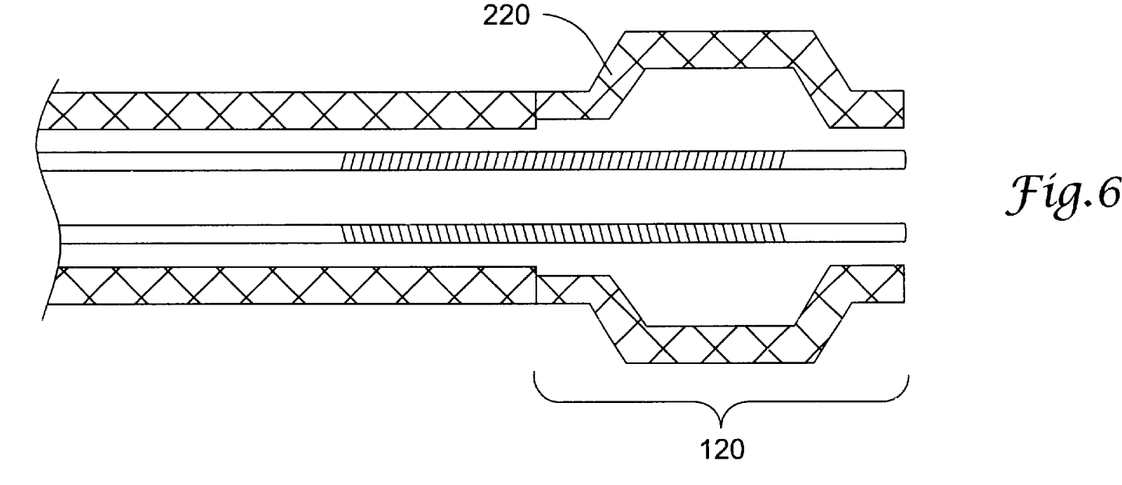
FIG. 6 is a schematic representation of the distal end of a catheter of this invention showing the braided reinforcing member extending from the distal end of the outer tube completely over the balloon-forming structure.
Figure 7:
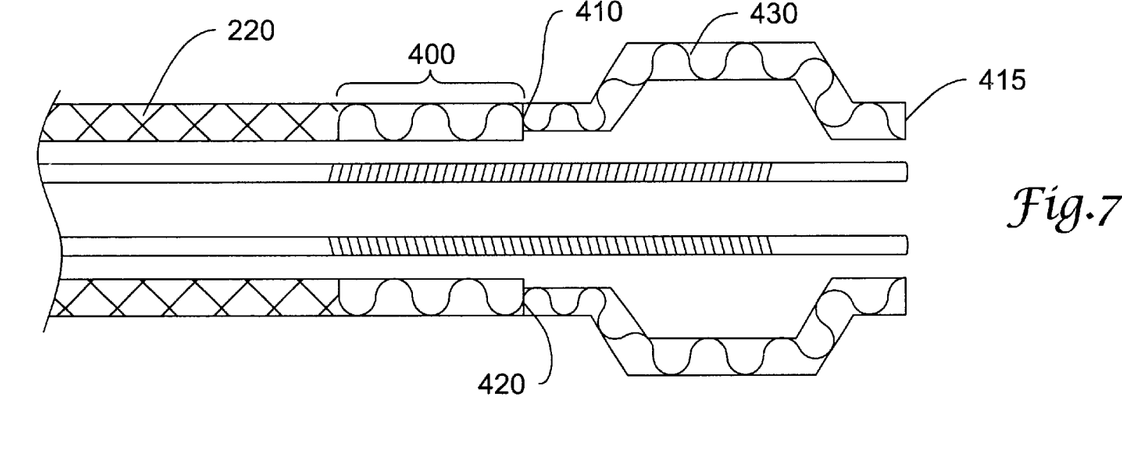
FIG. 7 is a schematic representation of the distal end of a catheter of this invention showing a separate reinforcing member extending from the distal end of the balloon-forming structure over the weld and onto the outer tube of the catheter.

It is also within the scope of this invention that braided member 220 extends completely over balloon-forming structure 120 to provide rupture resistance to the structure as shown in FIG. 6. To accommodate the increased diameter of balloon-forming structure 120 when inflated, the weave may be relaxed, that is, the distance between strands of braided reinforcing member 220 may be increased. Alternatively, balloon-forming structure 120 may incorporate a separate reinforcing member 430 that extends from its distal end 415 to beyond its proximal end 420, as shown in FIG. 7. Braided member 220 is then terminated at a distance 400 from the distal end 410 of tube 200. When proximal end 420 of balloon-forming structure 120 is bonded to the distal end 410 of tube 200, reinforcing member 430 can overlap the joint to provide additional strength and rupture resistance.

Figure 2C:
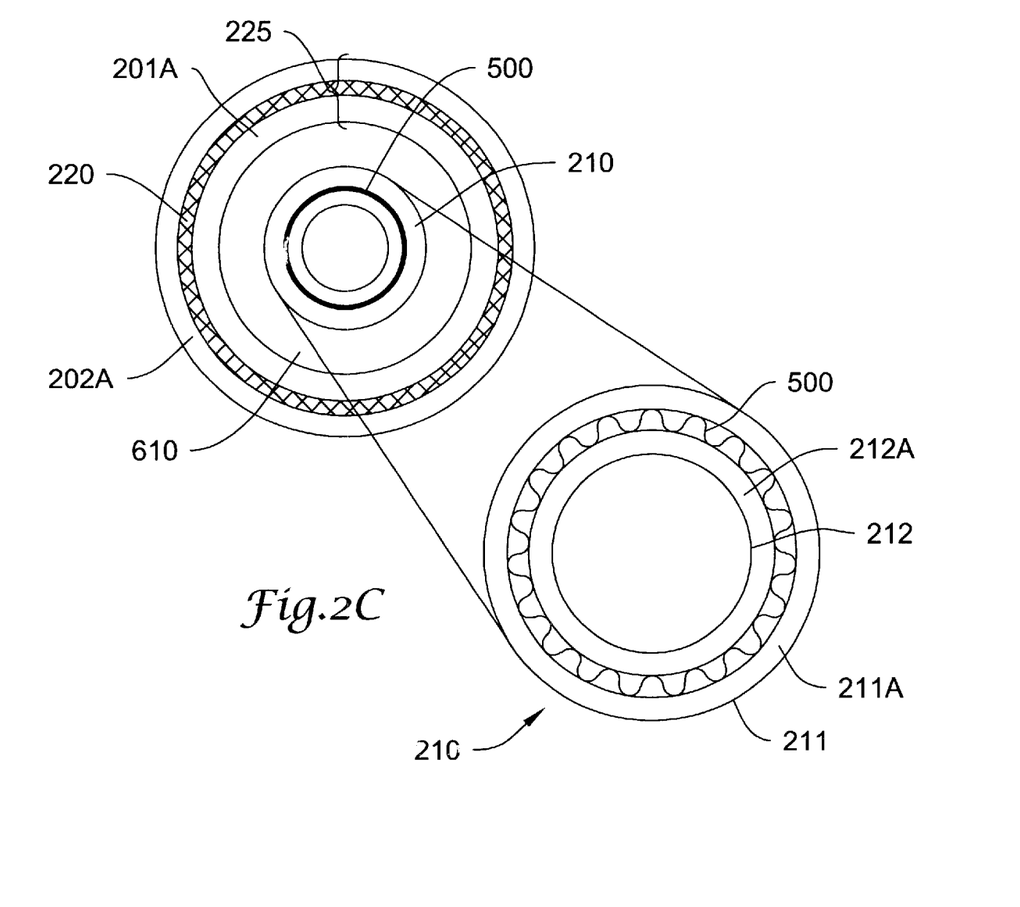
FIG. 2C is another schematic representation of a cross-section of the distal portion shown in FIG. 2A wherein the walls of the two tubes are depicted as layers of material.

Inner tube 210 (FIG. 2) is constructed similarly to outer tube 200. That is, inner tube 210 has an inner surface 212 and an outer surface 211. The two surfaces of may constructed of the same or of different materials, in the latter case the surfaces can be considered as comprising layers. That is, inner surface 212 may comprise the surface of a layer of material 212A and outer surface 211 may comprise the outer surface of a different layer of material 211 A. As before, the structure of tube 210 is not limited to any particular number of layers and the number and types of materials used can be varied depending on the characteristics to be imparted on tube 210. Disposed between surfaces 211 and 212 or layers 211A and 212 A is a reinforcing member 500 (FIGS. 2B, 2C). Reinforcing member 500 may be a braided member such as braided reinforcing member 220 in tube 200. In such case, reinforcing member 500 is likewise comprised of more than 4 individual braided strands each having a ribbon-like structure, that is, each strand has a cross-section having a width and a thickness where the width is greater than the thickness. The width and thickness of each strand are also similar to that of braided member 220. The materials from which reinforcing member 500 may be constructed are also the same as those described above for braided member 220. That is, the strands of reinforcing member 500 may be metallic or non-metallic. If metallic, the metals that may be used include, without limitation, stainless steel, platinum, palladium, gold, rhodium, tantalum and the like. In addition, metal alloys may also be used such as, again without limitation, nitinol (a titanium/nickel alloy). Non-metallic substances that can be used include, without limitation, aramids (e.g., KEVLAR), liquid crystal polymers and carbon fibers. In a catheter of this invention, the material from which reinforcing member 500 is constructed may be the same as that used to construct braided reinforcing member 220 or it may be another material selected from those described. When metallic strands are used to form reinforcing member 500, the dimensions of each strand are similar to those of each strand of braided reinforcing member 220. That is, each strand has a width of from about 0.002 inches to about 0.004 inches with about 0.003 inches being presently preferred. Likewise, when the strands are metallic, the thickness of each strand is from about 0.0004 to about 0.00075 inches with about 0.0005 inches being presently preferred.

Reinforcing member 500 need not, however, be braided. It may, for example be a single helically-wound strand. It may comprise a single helical wrap in one direction, proximal or distal or it may be wrapped in two directions, e.g., a first helical wrap going from proximal to distal and then a second wrap on top of the first going from distal to proximal. Jointly owned U.S. Pat. No. 6,152,912 describes such helically-wound reinforcing members and is incorporated by reference as if fully set forth herein.

Reinforcing member 500, like braided reinforcing member 220 is disposed between surface 211 and surface 212 or layers 211A and 212A of tube 210. If the two surfaces are made of the same material, reinforcing member 500 may simply be embedded in that material or a first layer of the material can be formed into a tube, reinforcing member 500 may then be wrapped around that tube and then additional material may be applied over reinforcing member 500 to complete the structure. If, on the other hand, surface 211 is of one material and surface 212 is of another such that tube 200 is made of at least two layers, 211A and 212A, reinforcing member 500 is sandwiched between them by wrapping layer 212A with reinforcing member 500 and than applying layer 211A over it. When tube 210 is constructed of layers of different substances, an adhesive may be used to assist in binding reinforcing member 500 to the layers the layers to one another.

As with tube 200, In order to accommodate reinforcing member 500 while maintaining a small overall cross-section, the thickness of the materials of which the wall of tube 210 is made must be reduced. In a presently preferred embodiment of this invention, inner layer 212A is necked down, either during manufacture or by subsequent laser milling, a braided reinforcing member is slid onto inner layer 212A and outer layer 211A is applied over the structure to encapsulate the braided reinforcing member.

Figure 8:
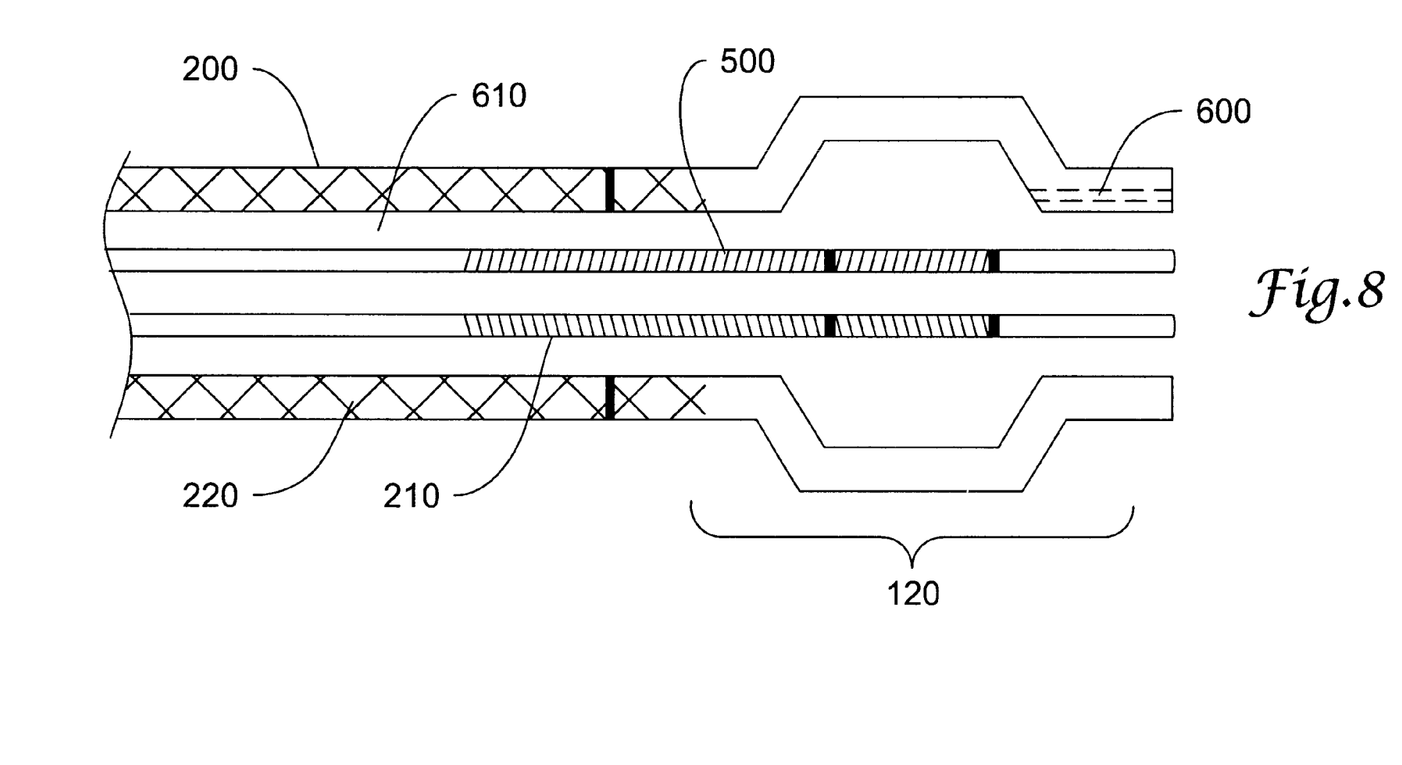
FIG. 8 is a schematic representation of a channel created in the distal end of the balloon forming structure to permit escape of air when the structure if filled with liquid to expand it.

It is also within the scope of this invention that each layer of tube 210 is constructed of different materials longitudinally as shown in FIG. 5 for tube 200 A final aspect of this invention is a channel 600 created at the distal end of the balloon-forming structure 120 (FIG. 8). The channel is constructed such that, when pressurized liquid is injected into annular space 610 between the outer surface 201 of tube 200 and the outer surface 212 of tube 210, any air trapped in the annular space is expelled through the channel. The channel is small enough, however, that the viscosity of the injected liquid keeps it from following the air through the channel resulting in deflation of balloon-forming structure 120. In addition, when liquid is being withdrawn from the annular space to collapse balloon-forming structure 120, usually by applying a vacuum to the system, channel 600 will also collapse thus preventing any significant amount of blood or other bodily fluid from being drawn into the annular space.

CONCLUSION

Thus, it will be appreciated that the devices disclosed herein will be useful in catheters, particularly the distal end of high-pressure vascular balloon catheters, wherein they will provide structural strength to resist bursting under pressure, torsional and longitudinal directivity and kink resistance while maintaining the small diametric profile necessary for traversing small tortuous vascular channels.

Although certain embodiments and examples have been used to describe the present invention, it will become apparent to those skilled in the art that changes in the embodiments and examples may be made without departing from the scope of the invention herein.

Other embodiments of this invention are within the following claims.

What is claimed is:

1. A high-pressure balloon catheter, comprising:
a first flexible elongate tubular member having a proximal end and a distal end, the first member having an outer surface and an inner surface that describes a lumen;
a second flexible elongate tubular member having a proximal end and a distal end, the second elongate member being disposed within the lumen of the first elongate tubular member and extending distally beyond the distal end of the first elongate member, the second member having an inner surface describing a lumen and an outer surface describing an outer diameter that is less than an inner diameter of the first elongate member such that an annular lumen is formed between the first and second elongate members;
an inflatable balloon-forming structure having a proximal end and a distal end, the structure being sealably coupled at its proximal end to the distal end of the first elongate member via a butt weld;
a first reinforcing member disposed between the inner and outer surfaces of the first elongate member, the first reinforcing member comprising a plurality of individual strands, each strand having a width and a thickness; and,
a second reinforcing member disposed between the inner and outer surfaces of the second elongate member;
wherein the first reinforcing member extends distally over the butt weld between the proximal end of the balloon-forming structure and the distal end of the first elongate member.

2. The catheter of claim 1, wherein the second reinforcing member extends from a point distal to the proximal end of the first member to a point distal to the proximate end of the balloon-forming structure.

3. The catheter of claim 2, wherein the second reinforcing member comprises a second braided reinforcing member.

4. The catheter of claim 3, wherein the second braided reinforcing member comprises a plurality of individual strands, each having a width and a thickness.

5. The catheter of claim 4, wherein the second braided reinforcing member is selected from the group consisting of a metal and a high tensile strength fiber.

6. The catheter of claim 5, wherein the metal is selected from the group consisting of nitinol and stainless steel.

7. The catheter of claim 5, wherein the high tensile strength fiber is selected from the group consisting of aramid, vertran, liquid crystal polymer and carbon fiber.

8. The catheter of claim 4, wherein the width of each strand of the second braided reinforcing member ranges from about 0.002 to about 0.004 inches.

9. The catheter of claim 4, wherein the thickness of each strand of the second braided reinforcing member ranges from about 0.0004 to about 0.00075 inches.

10. The catheter of claim 4, wherein the width of each strand of the second braided reinforcing member is about 0.003 inches and the thickness of each strand of the second braided reinforcing member is about 0.0005 inches.

11. The catheter of claim 1, wherein the first reinforcing member is a first braided reinforcing member.

12. The catheter of claim 11, wherein the width of each strand of the first braided reinforcing member ranges from about 0.002 to about 0.004 inches.

13. The catheter of claim 11, wherein the thickness of each strand of the first braided reinforcing member ranges from about 0.0004 to about 0.00075 inches.

14. The catheter of claim 11, wherein the width of each strand of the first braided reinforcing member is about 0.003 inches and the thickness of each strand of the first braided reinforcing member is about 0.0005 inches.

15. The catheter of claim 1, wherein the first reinforcing member is selected from the group consisting of a metal and a high tensile strength fiber.

16. The catheter of claim 15, wherein the metal is selected from the group consisting of nitinol and stainless steel.

17. The catheter of claim 15, wherein the high tensile strength fiber is selected from the group consisting of aramid, vertran, liquid crystal polymer and carbon fiber.

18. The catheter of claim 1, wherein the first braided reinforcing member extends over the balloon-forming structure to the distal end of the balloon-forming structure.

19. The catheter of claim 18, wherein the balloon-forming structure has an inner surface and an outer surface, the first reinforcing member being disposed between the inner and outer surfaces of the balloon-forming structure.

20. The catheter of claim 1, further comprising a channel located at the distal end of the balloon-forming structure, the channel operatively coupling an interior of the balloon-forming structure with an external environment.

21. A high-pressure balloon catheter, comprising:
a first flexible elongate tubular member having a proximal end and a distal end, the first member having an outer surface and an inner surface that describes a lumen;
a second flexible elongate tubular member having a proximal end and a distal end, the second elongate member being disposed within the lumen of the first elongate tubular member and extending distally beyond the distal end of the first elongate member, the second member having an inner surface describing a lumen and an outer surface describing an outer diameter that is less than an inner diameter of the first elongate member such that an annular lumen is formed between the first and second elongate members;
an inflatable balloon-forming structure having a proximal end and a distal end, the structure being sealably coupled at its proximal end to the distal end of the first elongate member;
a first reinforcing member disposed between the inner and outer surfaces of the first elongate member, the first reinforcing member comprising a plurality of individual strands, each strand having a width and a thickness; and
a second reinforcing member disposed between the inner and outer surfaces of the second elongate member;
wherein the first reinforcing member extends distally over the balloon-forming structure to the distal end of the balloon-forming structure.

22. A high-pressure balloon catheter, comprising:
a first flexible elongate tubular member having a proximal end and a distal end, the first member having an outer surface and an inner surface that describes a lumen;
a second flexible elongate tubular member having a proximal end and a distal end, the second elongate member being disposed within the lumen of the first elongate tubular member and extending distally beyond the distal end of the first elongate member, the second member having an inner surface describing a lumen and an outer surface describing an outer diameter that is less than an inner diameter of the first elongate member such that an annular lumen is formed between the first and second elongate members;

an inflatable balloon-forming structure having a proximal end and a distal end, the structure being sealably coupled at its proximal end to the distal end of the first elongate member;

a first reinforcing member disposed between the inner and outer surfaces of the first elongate member, the first reinforcing member comprising a plurality of individual strands, each strand having a width and a thickness; and a second reinforcing member disposed between the inner and outer surfaces of the second elongate member;

wherein the balloon-forming structure has an inner surface and an outer surface, and the first reinforcing member extends distally to the distal end of the balloon-forming structure and is disposed between the inner and outer surfaces of the balloon-forming structure.

23. A high-pressure balloon catheter, comprising:

a first flexible elongate tubular member having a proximal end and a distal end, the first member having an outer surface and an inner surface that describes a lumen;

a second flexible elongate tubular member having a proximal end and a distal end, the second elongate member being disposed within the lumen of the first elongate tubular member and extending distally beyond the distal end of the first elongate member, the second member having an inner surface describing a lumen and an outer surface describing an outer diameter that is less than an inner diameter of the first elongate member such that an annular lumen is formed between the first and second elongate members;

an inflatable balloon-forming structure having a proximal end and a distal end and an inner surface and an outer surface, the structure being sealably coupled at its proximal end to the distal end of the first elongate member;

a first reinforcing member disposed between the inner and outer surfaces of the first elongate member, the first reinforcing member comprising a plurality of individual strands, each strand having a width and a thickness; and a second reinforcing member disposed between the inner and outer surfaces of the second elongate member; and a third reinforcing member being disposed between the inner and outer surfaces of the balloon-forming structure from the distal end of the balloon-forming structure to a point proximal to the proximal end of the balloon-forming structure such that, when the proximal end of the balloon-forming structure is coupled to the distal end of the first elongate member, the third reinforcing member extends proximally over the coupling.

* * * * *